United States Patent
Tajima et al.

(10) Patent No.: US 11,813,341 B2
(45) Date of Patent: Nov. 14, 2023

(54) DENTAL PRODUCT WITH ENHANCED TOUGHNESS

(71) Applicant: KURARAY NORITAKE DENTAL INC., Kurashiki (JP)

(72) Inventors: Yuta Tajima, Aichi (JP); Toshio Sakakibara, Aichi (JP); Kiyoko Ban, Aichi (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 562 days.

(21) Appl. No.: 16/761,551

(22) PCT Filed: Nov. 6, 2018

(86) PCT No.: PCT/JP2018/041204
§ 371 (c)(1),
(2) Date: May 5, 2020

(87) PCT Pub. No.: WO2019/093334
PCT Pub. Date: May 16, 2019

(65) Prior Publication Data
US 2021/0169747 A1    Jun. 10, 2021

(30) Foreign Application Priority Data

Nov. 7, 2017  (JP) ................. 2017-214496

(51) Int. Cl.
| | |
|---|---|
| *A61K 6/818* | (2020.01) |
| *A61C 5/77* | (2017.01) |
| *A61K 6/20* | (2020.01) |
| *A61C 8/00* | (2006.01) |
| *C04B 41/50* | (2006.01) |
| *C04B 41/87* | (2006.01) |
| *A61K 6/58* | (2020.01) |
| *A61C 7/14* | (2006.01) |
| *A61C 13/083* | (2006.01) |
| *C04B 111/00* | (2006.01) |

(52) U.S. Cl.
CPC ............... *A61K 6/818* (2020.01); *A61C 5/77* (2017.02); *A61C 7/14* (2013.01); *A61C 8/0013* (2013.01); *A61K 6/20* (2020.01); *A61K 6/58* (2020.01); *C04B 41/5038* (2013.01); *C04B 41/87* (2013.01); *A61C 13/083* (2013.01); *C04B 2111/00836* (2013.01); *C04B 2237/348* (2013.01)

(58) Field of Classification Search
CPC ........ A61K 6/818; A61K 13/083; A61C 5/77; A61C 7/14; A61C 8/0013; C04B 41/87; C04B 41/86; C04B 41/3038; C04B 2111/00836; C04B 2237/348
See application file for complete search history.

(56) References Cited

U.S. PATENT DOCUMENTS

| | | | |
|---|---|---|---|
| 8,778,075 B2 | 7/2014 | Ritzberger et al. | |
| 2002/0197583 A1* | 12/2002 | Jones | A61K 6/893 433/201.1 |
| 2006/0099552 A1* | 5/2006 | van der Zel | C03C 4/0021 433/223 |
| 2006/0261503 A1* | 11/2006 | Sago | A61C 13/081 264/16 |
| 2011/0009254 A1 | 1/2011 | Schweiger et al. | |
| 2015/0374589 A1* | 12/2015 | Rampf | A61K 6/833 501/63 |

FOREIGN PATENT DOCUMENTS

| | | |
|---|---|---|
| JP | 10-323354 A | 12/1998 |
| JP | 2005-187436 A | 7/2005 |
| JP | 2017-122064 A | 7/2017 |
| JP | 2018-100229 A | 6/2018 |
| WO | WO 2014/034736 A1 | 3/2014 |

OTHER PUBLICATIONS

International Search Report dated Dec. 18, 2018 in PCT/JP2018/041204 filed Nov. 6, 2018, 1 page.
Extended European Search Report dated Jul. 7, 2021 in European Patent Application No. 18876683.6, 10 pages.

* cited by examiner

*Primary Examiner* — C Melissa Koslow
(74) *Attorney, Agent, or Firm* — Oblon, McClelland, Maier & Neustadt, L.L.P.

(57) ABSTRACT

The present invention provides a dental product comprising a base material formed of a zirconia sintered body, and having high aesthetic quality with enhanced fracture toughness and with reduced chipping and cracking in the porcelain layer. The present invention also provides a method for manufacturing such a dental product. The present invention relates to a dental product comprising: a base material formed of a zirconia sintered body, and a porcelain layer, wherein the porcelain of the porcelain layer has a suitable firing temperature of 900° C. or more, and the porcelain layer has a fracture toughness value of 1.20 MPa·m$^{0.5}$ or more.

13 Claims, 1 Drawing Sheet

DENTAL PRODUCT WITH ENHANCED TOUGHNESS

TECHNICAL FIELD

The present invention relates to a dental product comprising a zirconia sintered body, and to a method for manufacturing same.

BACKGROUND ART

For years, metal has been used for a range of dental products, including, for example, prostheses (such as veneer crowns, dental caps, crowns, and post crowns), orthodontic products, and products for dental implants. However, metals lack aesthetic quality because of the colors that are distinctively different from the color of natural teeth, and can cause allergic reaction when released from these products. These issues involving the use of metal have been addressed by dental products that use ceramic materials such as aluminum oxide (alumina) and zirconium oxide (zirconia) as alternative materials of metal. Comparatively, zirconia, in particular, has desirable strength and more appealing aesthetics, and this, combined with the current declining prices of zirconia, has created a high demand for this material.

For improved oral aesthetics, a dental product must match the appearance of natural teeth. It is, however, difficult to reproduce the appearance of natural teeth (particularly, transparency and gloss (luster)) with zirconia (sintered body) alone. This is overcome by fusing a ceramic material, called porcelain, into an exposed surface of a base zirconia material, instead of leaving the zirconia surface exposed, to provide more natural-looking dental products, for example, such as dental prostheses made to reproduce the appearance of natural teeth, and orthodontic products and dental implant products that look more harmonious with the natural dentition. For example, Patent Literatures 1 and 2 propose such dental products.

CITATION LIST

Patent Literature

Patent Literature 1: WO 2014/034736 A1
Patent Literature 2: JP 2017-122064 A

SUMMARY OF INVENTION

Technical Problem

A zirconia sintered body used for such a dental product has high fracture toughness in the base material itself made from the zirconia sintered body. However, the porcelain may fracture or come off at the porcelain-zirconia interface, and such a dental product cannot be necessarily said as having high fracture toughness as a composite material of zirconia and porcelain.

Patent Literature 1 addresses this issue by disclosing a method whereby a base material for a zirconia-porcelain composite is obtained by vacuum discharge plasma sintering of a mixture containing a zirconia powder and high-fusing porcelain in predetermined proportions. In this method, however, the porcelain contained in the mixture may interfere with crystal grain growth in firing of zirconia, and, because of the presence of porcelain in the spaces between zirconia crystals, chipping (break-off) or cracking may occur in the porcelain after repeated chewing. It is also easily imaginable that the hindered crystal grain growth that occurs during the zirconia firing process as a result of mixing porcelain into zirconia, and the presence of porcelain at the zirconia crystal grain boundary would result in firing and producing an opaque, clouded composite material that fails to satisfy the level of aesthetic quality that matches the appearance of natural teeth. Another issue is that the method requires a special type of device for firing performed under the particular conditions of discharge plasma sintering in a vacuum.

Patent Literature 2 describes a dental product having an improved fracture toughness value achieved by adjusting the porcelain composition. However, the porcelain in this dental product has a potential risk of chipping or other defects because of the low suitable firing temperature, and further improvements are needed for resistance against chipping, cracking, or detachment of the porcelain layer due to mastication.

It is accordingly an object of the present invention to provide a dental product comprising a base material formed of a zirconia sintered body, and having high aesthetic quality with enhanced fracture toughness and with reduced chipping and cracking in the porcelain layer. Another object of the present invention is to provide a method for manufacturing such a dental product.

Solution to Problem

The present inventors conducted intensive studies to find a solution to the foregoing issues, and found that the foregoing problems can be overcome by using a porcelain layer having a specific range of suitable firing temperature, or by firing the porcelain in a specific temperature range. The present invention was completed after further studies on the basis of this finding.

Specifically, the present invention relates to the following:
[1] A dental product comprising: a base material formed of a zirconia sintered body, and a porcelain layer, wherein the porcelain of the porcelain layer has a suitable firing temperature of 900° C. or more, and the porcelain layer has a fracture toughness value of 1.20 MPa·m$^{0.5}$ or more;
[2] The dental product according to [1], wherein the porcelain layer has a thickness of 10 to 500 μm;
[3] The dental product according to [1] or [2], wherein the base material formed of a zirconia sintered body comprises a stabilizer;
[4] The dental product according to [3], wherein the stabilizer is at least one selected from the group consisting of yttrium oxide, titanium oxide, calcium oxide, magnesium oxide, cerium oxide, aluminum oxide, scandium oxide, lanthanum oxide, erbium oxide, praseodymium oxide, samarium oxide, europium oxide, and thulium oxide;
[5] The dental product according to any one of [1] to [4], wherein the suitable firing temperature of the porcelain is 1,100° C. or more;
[6] The dental product according to any one of [1] to [5], wherein the dental product satisfies the following relation, 0<{(coefficient of thermal expansion of the porcelain)/(coefficient of thermal expansion of the zirconia sintered body)}<1.0;

[7] The dental product according to [6], wherein the dental product satisfies the following relation, $1.0 \times 10^{-6} K^{-1}$ ≤(coefficient of thermal expansion of the zirconia sintered body)−(coefficient of thermal expansion of the porcelain)≤$4.5 \times 10^{-6} K^{-1}$;

[8] A method for manufacturing the dental product of any one of [1] to [7], comprising the step of forming a porcelain layer on a zirconia sintered body, and firing the porcelain layer at a temperature of 1,350° C. or more;

[9] A method for manufacturing the dental product of any one of [1] to [7], comprising the step of forming a porcelain layer on a zirconia pre-sintered body, and firing the zirconia pre-sintered body and the porcelain layer at a temperature equal to or greater than a suitable firing temperature of the zirconia pre-sintered body;

[10] The dental product according to any one of [1] to [7], wherein the dental product is at least one selected from the group consisting of a dental prosthesis, an orthodontic product, and a product for dental implants.

Advantageous Effects of Invention

With the present invention, a dental product can be provided that comprises a base material formed of a zirconia sintered body, and that has high aesthetic quality with enhanced fracture toughness and with reduced chipping and cracking in the porcelain layer. The present invention can also provide a method for manufacturing such a dental product. This has made it possible to provide dental prostheses, orthodontic products, and products for dental implants that are highly resistant to chipping and cracking while maintaining high aesthetic quality. A dental product of the present invention does not involve mixing of porcelain in the base material, and the porcelain does not chip (break off) or crack after repeated chewing.

DESCRIPTION OF EMBODIMENTS

Figure 1:
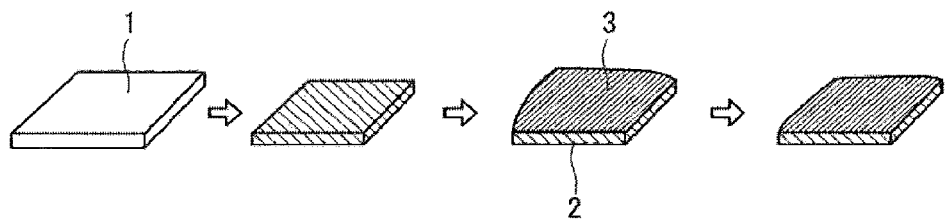
FIG. 1 is a diagram schematically representing a dental product manufacturing method of the present invention.
Figure 1:
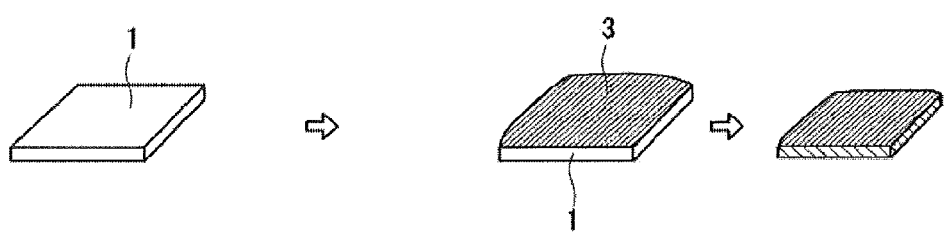

A dental product of the present invention is a dental product comprising: a base material formed of a zirconia sintered body, and a porcelain layer, wherein the porcelain of the porcelain layer has a suitable firing temperature of 900° C. or more, and the porcelain layer has a fracture toughness value of 1.20 MPa·m. or more.

The base material formed of a zirconia sintered body is described first. The base material is a material containing zirconia ($ZrO_2$; zirconium oxide) as a main component (predominant component), and that is obtained upon firing zirconia after the material is turned into the shape of a dental product to be produced. For example, in the case of a dental prosthesis or a product for dental implants, the base material may be fabricated from a disc or a block obtained by pressing a zirconia powder using a known technique.

Preferably, the base material comprises a stabilizer because the base material, as a dental product, requires the levels of chipping resistance, crack resistance, and bend strength sufficient to withstand repeated mastication. Specifically, it is preferable to add a stabilizer to zirconia before firing. In this way, a zirconia sintered body that turns into the base material can have a matrix phase that is preferably at least one of partially stabilized zirconia and fully stabilized zirconia. In the zirconia sintered body, the primary crystalline phase of zirconia is at least one of tetragonal crystal and cubical crystal. The primary crystalline phase of zirconia may contain both tetragonal crystal and cubical crystal. Preferably, the zirconia sintered body is essentially free of monoclinic crystals. Here, "essentially free of monoclinic crystals" means that the zirconia sintered body has a monoclinic crystal content of less than 5.0 mass %, preferably less than 1.0 mass %. As is known, partially stabilized zirconia (PSZ) refers to zirconia that is partially stabilized by addition of a stabilizer, and fully stabilized zirconia refers to zirconia fully stabilized with a stabilizer.

The stabilizer is preferably at least one oxide selected from the group consisting of yttrium oxide ($Y_2O_3$; hereinafter, "yttria"), titanium oxide ($TiO_2$), calcium oxide (calcia; CaO), magnesium oxide (magnesia; MgO), cerium oxide (ceria; $CeO_2$), aluminum oxide (alumina; $Al_2O_3$), scandium oxide ($Sc_2O_3$), lanthanum oxide ($La_2O_3$), erbium oxide ($Er_2O_3$), praseodymium oxide ($Pr_6O_{11}$), samarium oxide ($Sm_2O_3$), europium oxide ($Eu_2O_3$), and thulium oxide ($Tm_2O_3$). In view of high translucency and improved strength, preferred as stabilizer is yttria. These may be used alone, or two or more thereof may be used in combination.

When the stabilizer is containing yttria, the yttria content is preferably 2 to 8 mol %, more preferably 3 to 6 mol % of total 100 mol % of zirconia and stabilizer. With these contents, a phase transition to monoclinic crystals can be suppressed, and the zirconia sintered body can have improved transparency.

When titanium oxide is contained as a stabilizer, the content of titanium oxide is preferably 0.1 to 1 mol %, more preferably 0.1 to 0.3 mol % of total 100 mol % of zirconia and stabilizer.

When calcium oxide is contained as a stabilizer, the content of calcium oxide is preferably 2 to 15 mol %, more preferably 2.1 to 12 mol % of total 100 mol % of zirconia and stabilizer.

When magnesium oxide is contained as a stabilizer, the content of magnesium oxide is preferably 2 to 12 mol %, more preferably 2.1 to 10 mol % of total 100 mol % of zirconia and stabilizer.

When cerium oxide is contained as a stabilizer, the content of cerium oxide is preferably 2 to 18 mol %, more preferably 2.1 to 12 mol % of total 100 mol % of zirconia and stabilizer.

When aluminum oxide is contained as a stabilizer, the content of aluminum oxide is preferably 0.1 to 1 mol %, more preferably 0.1 to 0.3 mol % of total 100 mol % of zirconia and stabilizer.

When scandium oxide is contained as a stabilizer, the content of scandium oxide is preferably 0.1 to 1 mol %, more preferably 0.1 to 0.3 mol % of total 100 mol % of zirconia and stabilizer.

When lanthanum oxide is contained as a stabilizer, the content of lanthanum oxide is preferably 1 to 10 mol %, more preferably 2 to 7 mol % of total 100 mol % of zirconia and stabilizer.

When erbium oxide is contained as a stabilizer, the content of erbium oxide is preferably 0.1 to 1 mol %, more preferably 0.1 to 0.3 mol % of total 100 mol % of zirconia and stabilizer.

When praseodymium oxide is contained as a stabilizer, the content of praseodymium oxide is preferably 0.1 to 1 mol %, more preferably 0.1 to 0.3 mol % of total 100 mol % of zirconia and stabilizer.

When samarium oxide is contained as a stabilizer, the content of samarium oxide is preferably 0.1 to 1 mol %, more preferably 0.1 to 0.3 mol % of total 100 mol % of zirconia and stabilizer.

When europium oxide is contained as a stabilizer, the content of europium oxide is preferably 0.1 to 1 mol %, more preferably 0.1 to 0.3 mol % of total 100 mol % of zirconia and stabilizer.

When thulium oxide is contained as a stabilizer, the content of thulium oxide is preferably 0.1 to 1 mol %, more preferably 0.1 to 0.3 mol % of total 100 mol % of zirconia and stabilizer.

The content of the stabilizer in the zirconia sintered body can be measured using a technique, for example, such as inductively coupled plasma (ICP) emission spectral analysis or x-ray fluorescence analysis.

The shape and size (dimensions) of the base material can be appropriately selected according to factors such as use, and the patient's oral environment.

The following describes the porcelain. As used herein, "porcelain" means a powdery material in which sinterable ceramic, glass, or glass-ceramic (crystallized glass) commonly used for fabrication of dental caps is contained as a main component (predominant component). In a dental product of the present invention, porcelain is used as a porcelain layer that covers at least a part of the base material formed of a zirconia sintered body.

In the present invention, the porcelain has a suitable firing temperature of 900° C. or more, preferably 950° C. or more, more preferably 1,000° C. or more, even more preferably 1,050° C. or more, particularly preferably 1,100° C. or more, most preferably 1,300° C. or more. A suitable firing temperature of less than 900° C. may result in decrease of fracture toughness value (described later), and can lead to chipping or cracking. A porcelain with a suitable firing temperature of less than 900° C. may produce a porcelain layer that appears cloudy, and severely impairs the aesthetic quality of the dental product. The upper limit of suitable firing temperature is preferably, for example, 1,600° C. or less, though it is not particularly limited. The suitable firing temperature of the porcelain may be adjusted according to the distribution of the components constituting the porcelain (described below). In this specification, the suitable firing temperature of porcelain can be measured using the method described in the EXAMPLES section.

The porcelain is produced as follows. First, a raw mixture of the desired composition is produced by mixing compounds containing elements such as Si, Al, Li, Na, K, Ca, Mg, Ba, Zn, B, Ce, and F. For example, the raw mixture for porcelain production preferably contains oxides such as $SiO_2$, $Al_2O_3$, $Li_2O$, $Na_2O$, $K_2O$, CaO, MgO, BaO, ZnO, $B_2O_3$, and $CeO_2$, and a compound (for example, $AlF_3$ or $BaF_2$) that generates $F_2$ by undergoing pyrolysis.

The composition of the raw mixture for porcelain is not limited to these compounds, and other compounds, for example, such as carbonates, nitrates, hydroxides, and fluorides of elements such as above may be used, provided that the desired composition is obtained. The mass composition of the raw mixture may be appropriately varied according to the compounds used. The raw mixture can be obtained by mixing the compounds using, for example, a ball mill.

The raw mixture (composition) is heated to melt. The melt is cooled into a cullet, and the cullet is pulverized using a ball mill. The pulverized particles are sieved through, for example, a #200 mesh sieve. The porcelain of the present invention can be produced through these steps. For melting, a temperature of, for example, about 1,400° C. to 1,600° C. may be applied. The duration of melting may be about 2 to 6 hours.

Preferably, the components that constitute the porcelain of the present invention comprise $SiO_2$, $Al_2O_3$, $Na_2O$, $K_2O$, and CaO. The content of $SiO_2$ in the porcelain is, for example, preferably 65.0 to 90.0 mol %, more preferably 67.0 to 89.5 mol %, even more preferably 69.8 to 88.7 mol % of total 100 mol % of the constituent components. The content of $Al_2O_3$ in the porcelain is, for example, preferably 4.0 to 15.0 mol %, more preferably 5.6 to 14.5 mol %, even more preferably 5.7 to 12.7 mol % of total 100 mol % of the constituent components. The content of $Na_2O$ in the porcelain is, for example, preferably 0.1 to 10.0 mol %, more preferably 1.0 to 7.0 mol %, even more preferably 1.7 to 3.8 mol % of total 100 mol % of the constituent components. The content of $K_2O$ in the porcelain is, for example, preferably 1.0 to 10.0 mol %, more preferably 2.5 to 9.5 mol %, even more preferably 3.6 to 8.3 mol % of total 100 mol % of the constituent components. The content of CaO in the porcelain is, for example, preferably 0.01 to 15.0 mol %, more preferably 0.05 to 13.5 mol %, even more preferably 0.1 to 12.2 mol % of total 100 mol % of the constituent components. The suitable firing temperature of porcelain can be confined within the appropriate range by adjusting the content of each constituent component. $SiO_2$, $Al_2O_3$, and CaO tend to raise the suitable firing temperature of porcelain, whereas $Na_2O$ and $K_2O$ tend to lower the suitable firing temperature of porcelain.

In view of enhancing fracture toughness and reducing chipping and cracking of the porcelain layer while ensuring high aesthetic quality, it is preferable in the porcelain of the present invention that the content of $K_2O$ (number of moles) be greater than the content of $Na_2O$ (number of moles). Specifically, the porcelain of the present invention satisfies preferably $1.0<\{$(number of moles of $K_2O$)/(number of moles of $Na_2O$)$\}$, more preferably $1.5<\{$(number of moles of $K_2O$)/(number of moles of $Na_2O$)$\}$, even more preferably $2.0<\{$(number of moles of $K_2O$)/(number of moles of $Na_2O$)$\}$. The upper limit value of $\{$(number of moles of $K_2O$)/(number of moles of $Na_2$)$\}$, specifically, the upper limit of the mole ratio of $K_2O$ and $Na_2O$, is not particularly limited, and may be less than 100, less than 50, or less than 30.

The components that constitute the porcelain of the present invention may further comprise at least one component selected from the group consisting of $Li_2O$, MgO, BaO, ZnO, $B_2O_3$, $CeO_2$, and $F_2$, or may be essentially free of these components. The content of $Li_2O$ in the porcelain is, for example, preferably 0.0 to 3.5 mol %, more preferably 0.1 to 3.0 mol %, even more preferably 0.2 to 2.0 mol % of total 100 mol % of the constituent components. The content of MgO in the porcelain is, for example, preferably 0.0 to 3.5 mol %, more preferably 0.1 to 3.0 mol %, even more preferably 0.2 to 2.0 mol % of total 100 mol % of the constituent components. The content of BaO in the porcelain is, for example, preferably 0.0 to 3.5 mol %, more preferably 0.1 to 3.0 mol %, even more preferably 0.2 to 2.0 mol % of total 100 mol % of the constituent components. The content of ZnO in the porcelain is, for example, preferably 0.0 to 3.5 mol %, more preferably 0.1 to 3.0 mol %, even more preferably 0.2 to 2.0 mol % of total 100 mol % of the constituent components. The content of $B_2O_3$ in the porcelain is, for example, preferably 0.0 to 3.5 mol %, more preferably 0.1 to 3.0 mol %, even more preferably 0.2 to 2.0 mol % of total 100 mol % of the constituent components. In view of inhibiting decrease of suitable firing temperature, it is preferable that the porcelain of the present invention be essentially free of $B_2O_3$. The content of $CeO_2$ in the porcelain is, for example, preferably 0.0 to 3.5 mol %, more preferably 0.1 to 3.0 mol %, even more preferably 0.2 to 2.0 mol % of total 100 mol % of the constituent components. The content of $F_2$ in the porcelain is, for example, preferably 0.0 to 5.0 mol %, more preferably 0.1 to 3.0 mol %, even more preferably 0.15 to 2.5 mol % of total 100 mol % of the constituent components. The porcelain of the present invention may comprise SrO. The porcelain of the present invention may comprise about 0.1 to 3.0 mol % of a trace component, such as $ZrO_2$, $SnO_2$, or $TiO_2$, relative to total 100 mol % of the constituent components, or may be essentially free of these components. As used herein, "essentially free of a component" means that the content of the component is less than 0.1 mol %, preferably less than 0.05 mol %, particularly preferably less than 0.01 mol %.

The porcelain layer of the present invention comprises the porcelain as a main component (predominant component), and covers at least a part of the base material formed of a zirconia sintered body.

The porcelain layer of the present invention has a thickness of preferably 10 to 500 µm, more preferably 10 to 200 µm. With the porcelain layer having a thickness of 10 to 500 µm, the base material formed of a zirconia sintered body, itself, will not be exposed in parts of the surface of the dental product, producing an evenly glossy appearance that matches natural teeth, particularly in transparency and glossiness (luster). The thickness of the porcelain layer can be measured by measuring the fired porcelain with a micrometer.

The porcelain layer of the present invention has a fracture toughness value of 1.20 MPa·m$^{0.5}$ or more. The fracture toughness value of the porcelain layer is preferably 1.25 MPa·m$^{0.5}$ or more, more preferably 1.30 MPa·m$^{0.5}$, even more preferably 1.35 MPa·m$^{0.5}$. With the porcelain layer having a fracture toughness value of 1.20 MPa·m$^{0.5}$ or more, the dental product produced can have desirable resistance against chipping, cracking, or detachment of the porcelain layer. In this specification, the fracture toughness value of the porcelain layer can be measured using the method described in the EXAMPLES section below.

It is preferable in the dental product of the present invention that the porcelain have a smaller coefficient of thermal expansion (hereinafter, also referred to as "CTE") than the zirconia sintered body forming the base material. Specifically, it is preferable that the dental product satisfy {(CTE of porcelain after firing)/(CTE of zirconia sintered body)}<1.0. In this specification, the coefficients of thermal expansion of the porcelain and the zirconia sintered body can be measured by measuring the fired porcelain in an analysis temperature range of 25° C. to 500° C. in compliance with ISO 6872:2015, as will be described later in detail in EXAMPLES below.

The coefficient of thermal expansion difference between the zirconia sintered body and the porcelain is preferably $1.0 \times 10^{-6} K^{-1}$ to $4.5 \times 10^{-6} K^{-1}$, more preferably $1.5 \times 10^{-6} K^{-1}$ to $4.5 \times 10^{-6} K^{-1}$, even more preferably $2.0 \times 10^{-6} K^{-1}$ to $3.5 \times 10^{-6} K^{-1}$. As stated above, in the present invention, the coefficient of thermal expansion of the zirconia sintered body is preferably greater than the coefficient of thermal expansion of the porcelain after firing, and, accordingly, the coefficient of thermal expansion difference is typically represented by (coefficient of thermal expansion of zirconia sintered body)–(coefficient of thermal expansion of porcelain after firing). By setting a coefficient of thermal expansion difference of $1.0 \times 10^{-6} K^{-1}$ to $4.5 \times 10^{-6} K^{-1}$ for the zirconia sintered body and the fired porcelain in the foregoing configuration that includes confining the suitable firing temperature of porcelain within the foregoing predetermined ranges, the porcelain layer covering at least a part of the zirconia sintered body experiences compressional stress created by the coefficient of thermal expansion difference. This makes it possible to further increase fracture toughness, and reduce chipping or cracking.

The fracture toughness enhancing effect becomes even greater when the coefficient of thermal expansion difference between the zirconia sintered body and the porcelain is $1.0 \times 10^{-6} K^{-1}$ or more. With a coefficient of thermal expansion difference of $4.5 \times 10^{-6} K^{-1}$ or less, the dental product becomes even less likely to crack because of the absence of excessive stress on the zirconia sintered body and the porcelain. The coefficient of thermal expansion of the zirconia sintered body varies with, for example, the content of the stabilizer (e.g., yttria). In the case of a zirconia sintered body having a yttria content of 2 to 8 mol % typically used in dental applications, the coefficient of thermal expansion is about $10 \times 10^{-6} K^{-1}$.

The following two methods are examples of a dental product manufacturing method of the present invention:

(1) A method comprising the step of forming a porcelain layer on a zirconia sintered body, and firing the porcelain layer at a temperature of 1,350° C. or more.
(2) A method comprising the step of forming a porcelain layer on a zirconia pre-sintered body, and firing the zirconia pre-sintered body and the porcelain layer at a temperature equal to or greater than a suitable firing temperature of the zirconia pre-sintered body.

These are described below, with reference to FIG. 1.

In manufacturing method (1), for example, a zirconia sintered body 2 may be obtained by forming a zirconia powder (preferably, a zirconia powder containing the stabilizer) under a predetermined pressure, and pre-sintering the resulting zirconia compact and firing the resultant zirconia pre-sintered body 1. The zirconia pre-sintered body 1 may be fired at, for example, about 1,300 to 1,600° C., though the temperature is not particularly limited. The zirconia pre-sintered body may be fired for, for example, about 30 minutes to 8 hours. Preferably, a porcelain layer 3 is formed on the zirconia sintered body 2, and fired at a temperature of 1,350° C. or more. By firing the porcelain layer 3 at a temperature of 1,350° C. or more, a dental product can be obtained that has desirable resistance against chipping, cracking, and detachment of the porcelain layer 3 while ensuring high aesthetic quality. The upper limit of porcelain firing temperature is not particularly limited, as long as the present invention can produce its effects. For example, the porcelain firing temperature is 1,600° C. or less. The porcelain may be fired for, for example, about 30 seconds to 8 hours. The zirconia pre-sintered body 1 may be a commercially available product. Pre-sintering of the zirconia compact, and firing of the zirconia pre-sintered body and porcelain may be performed using known techniques and devices.

In manufacturing method (2), a zirconia pre-sintered body 1 may be obtained from a zirconia powder as in manufacturing method (1), or may be a commercially available product, specific examples of which include Noritake KATANA™ zirconia KT, Noritake KATANA™ zirconia HT/ML, Noritake KATANA™ zirconia STML, and Noritake KATANA™ zirconia UTML (all manufactured by Kuraray Noritake Dental Inc.), and Bellezza Hi-Trans Zirconia manufactured by Nissin Dental Products Inc. Preferably, a porcelain layer 3 is formed on the zirconia pre-sintered body 1, and the zirconia pre-sintered body 1 and the porcelain are fired at a temperature equal to or greater than the suitable firing temperature of the zirconia pre-sintered body 1. By simultaneously firing the zirconia pre-sintered body 1 and the porcelain layer 3 at a temperature equal to or greater than the suitable firing temperature of the zirconia pre-sintered body 1, a dental product can be obtained that has desirable resistance against chipping, cracking, and detachment of the porcelain layer while ensuring high aesthetic quality. In this specification, the suitable firing temperature of zirconia pre-sintered body can be measured using the method described in the EXAMPLES section below. The upper limit of the firing temperature for zirconia pre-sintered body and porcelain is not particularly limited, and may be, for example, 1,600° C. or less. The zirconia pre-sintered body and porcelain may be fired for, for example, about 30 minutes to 8 hours. Firing of the zirconia pre-sintered body and porcelain may be performed using known techniques and devices.

The following describes an example of a method for producing the zirconia pre-sintered body 1 used in manufacturing methods (1) and (2). First, a raw material granule of zirconia containing a stabilizer is prepared, and pressed into, for example, a block or a disc shape. Optionally, the resulting zirconia compact is subjected to cold isostatic pressing (CIP). The applied pressure is, for example, 50 to 500 MPa. This is followed by pre-sintering. In pre-sintering, the temperature is gently increased from room temperature to 800 to 1,200° C. and the zirconia compact is held for about 1 to 6 hours to obtain a zirconia pre-sintered body. As a final step, the zirconia pre-sintered body is fired into the zirconia sintered body at the suitable temperature specified by manufacturing method (1) or (2). The zirconia sintered body of the present invention not just limited to sintered bodies produced by firing molded zirconia particles under ordinary pressure or no applied pressure, and includes sintered compacts produced by high-temperature pressing such as hot isostatic pressing (HIP).

The method for forming the porcelain layer in manufacturing methods (1) and (2) is not particularly limited, and the porcelain layer may be formed by using a known method, for example, such as coating (e.g., coating with a brush), spraying, or dipping. For example, porcelain (powder) is dispersed in a solvent to prepare a slurry, and the slurry is applied to the zirconia sintered body in the case of manufacturing method (1), and to the zirconia pre-sintered body in the case of manufacturing method (2). The solvent may be, for example, water, an organic solvent, or a mixed solvent of these. Examples of the organic solvent include 2-phenoxyethanol, propylene glycol, 1,3-butanediol, and glycerin.

A dental product of the present invention is applicable to a range of products, including dental prostheses, orthodontic products, and products for dental implants. Examples of the dental prostheses include crowns, crown bridges, denture bases, inlays, onlays, and laminate veneers. Examples of the orthodontic products include brackets. Examples of the products for dental implants include implants and implant bridges.

The present invention encompasses combinations of the foregoing features, provided that such combinations made in various forms within the technical idea of the present invention can produce the effects of the present invention.

EXAMPLES

The following describes the present invention in greater detail by way of Examples. It should be noted that the present invention is in no way limited by the following Examples, and various changes may be made by a person with ordinary skill in the art within the technical idea of the present invention.

Production Examples 1 to 5: Fabrication of Porcelain

The porcelains used in Examples and Comparative Examples were produced as follows. First, raw mixtures of the compositions shown in Table 1 were prepared by mixing $SiO_2$, $Al_2O_3$, $Li_2O$, $Na_2O$, $K_2O$, CaO, MgO, ZnO, $B_2O_3$, and $CeO_2$ containing Si, Al, Li, Na, K, Ca, Mg, Zn, B, and Ce. Each raw mixture (composition) was heated to melt, and the melt was cooled and formed into a cullet. The cullet was then pulverized with a ball mill. The pulverized particles were sieved through a #200 mesh sieve to obtain a porcelain powder. For melting, a temperature of 1,500° C. was applied for 120 minutes.

Evaluation of Suitable Firing Temperature of Porcelain

Figure 2:
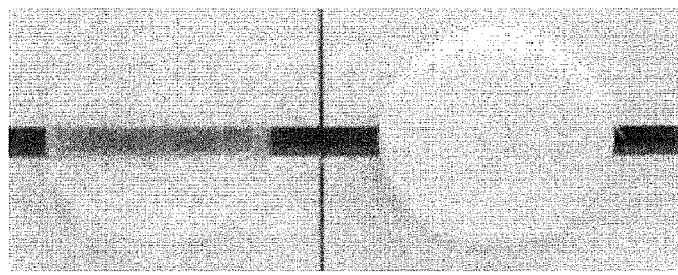
FIG. 2 is a photograph showing the appearance of porcelain in relation to determination of a suitable firing temperature of porcelain according to the present invention.

A slurry of each porcelain powder obtained in Production Examples 1 to 5 was produced using purified water. The porcelain slurry was poured into a mold measuring about 13 mm in diameter and about 1.5 mm in thickness, and dried to prepare a cylindrical solid specimen. The solid specimen was then fired using Cerafusion BX, a furnace manufactured by SK medical electronics Co., Ltd. After firing, the appearance of the cylindrical porcelain was observed with a digital microscope KH-7700 manufactured by Hirox Co., Ltd. The suitable firing temperature of each porcelain was determined from the surface roughness and transparency of the fired porcelain, using the following criteria. The porcelain can be determined as being sufficiently fired when it has a smooth surface, and transparency clear enough to show the background, as shown on the left-hand side of the picture in FIG. 2. On the other hand, firing can be determined as being insufficient when the porcelain has a rough surface with low transparency, as shown on the right-hand side of the picture in FIG. 2. In the present invention, the lowest temperature at which the porcelain can be regarded as being sufficiently fired as in the left porcelain in FIG. 2 was determined as the suitable firing temperature of the porcelain. The suitable firing temperatures of the porcelains of Production Examples 1 to 5 are shown in Table 1.

Measurement of Coefficient of Thermal Expansion of Porcelain

Coefficient of thermal expansion was measured in compliance with ISO 6872:2015. First, a slurry of each porcelain powder obtained in Production Examples 1 to 5 was produced using purified water. The slurry was poured into a mold of a size that meets the foregoing ISO standards, and dried to produce a prism-shaped specimen. The prism-shaped specimen was fired for 1 minute at the suitable firing temperature shown in Table 1, using Cerafusion BX, a furnace manufactured by SK medical electronics Co., Ltd. After firing, the dimensions of the prism-shaped specimen were adjusted according to the foregoing ISO standards to prepare a specimen for coefficient of thermal expansion measurement. The coefficient of thermal expansion was analyzed in a temperature range of 25° C. to 500° C. Measurements were taken by increasing temperature at a rate of 10K/min. A thermomechanical analyzer (Thermo plus TMA8310, manufactured by Rigaku Corporation) was used for measurement. The coefficients of thermal expansion of the porcelains of Production Examples 1 to 5 are shown in Table 1.

TABLE 1

|  |  | Production Example 1 | Production Example 2 | Production Example 3 | Production Example 4 | Production Example 5 |
|---|---|---|---|---|---|---|
| Porcelain composition (mol %) | $SiO_2$ | 88.7 | 75.2 | 72.6 | 74.6 | 75.2 |
|  | $Al_2O_3$ | 5.7 | 12.6 | 12.6 | 6.5 | 3.5 |
|  | $Li_2O$ | 0.0 | 0.0 | 0.0 | 0.0 | 2.0 |
|  | $Na_2O$ | 1.7 | 3.8 | 2.7 | 9.1 | 7.9 |
|  | $K_2O$ | 3.8 | 8.3 | 6.0 | 6.5 | 6.3 |
|  | $CaO$ | 0.1 | 0.1 | 6.1 | 3.0 | 1.1 |
|  | $MgO$ | 0.0 | 0.0 | 0.0 | 0.0 | 0.1 |
|  | $ZnO$ | 0.0 | 0.0 | 0.0 | 0.0 | 0.9 |
|  | $B_2O_3$ | 0.0 | 0.0 | 0.0 | 0.0 | 2.2 |
|  | $CeO_2$ | 0.0 | 0.0 | 0.0 | 0.3 | 0.8 |
| Properties of porcelain | Suitable firing temperature (° C.) | 1450 | 1350 | 1200 | 800 | 850 |
|  | Coefficient of thermal expansion ($\times 10^{-6} K^{-1}$) | 5.4 | 7.1 | 6.1 | 8.9 | 8.8 |

Evaluation of Suitable Firing Temperature of Zirconia Pre-Sintered Body

Figure 3:
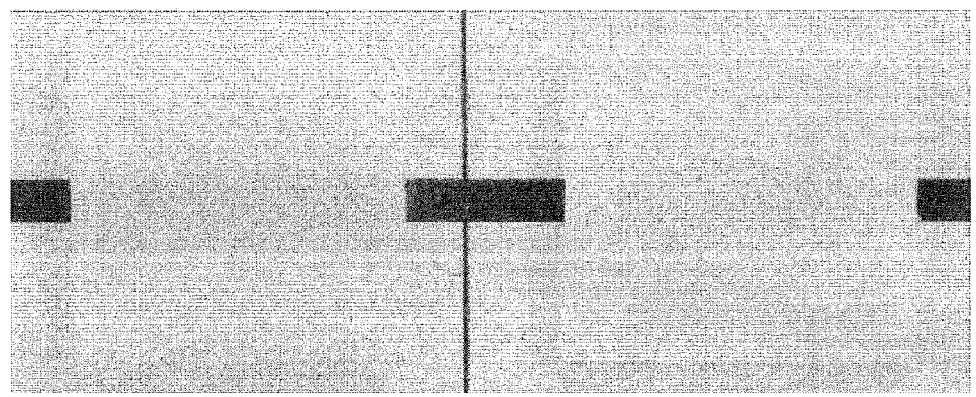
FIG. 3 is a photograph showing the appearance of a zirconia pre-sintered body in relation to determination of a suitable firing temperature of the zirconia pre-sintered body according to the present invention.

A zirconia pre-sintered body was cut into a specimen having a thickness of about 1.5 mm, and was fired using Noritake KATANA™ F-1N, a furnace manufactured by SK medical electronics Co., Ltd. The specimen may be quadrangular or circular in shape. Here, the specimen was prepared from the zirconia pre-sintered body in such a manner that the specimen had a thickness of about 1.2 mm after firing. The appearance of the specimen was observed by visual inspection, and the suitable firing temperature of the zirconia pre-sintered body was determined from the transparency of the specimen, using the following criteria. The zirconia pre-sintered body can be determined as being sufficiently fired when the specimen has transparency clear enough to show the background, as shown on the left-hand side of the picture in FIG. 3. On the other hand, firing can be determined as being insufficient when the specimen is low in transparency or appears cloudy, as shown on the right-hand side of the picture in FIG. 3. In the present invention, the lowest temperature at which the zirconia pre-sintered body can be regarded as being sufficiently fired as in the left specimen in FIG. 3 was determined as the suitable firing temperature of the zirconia pre-sintered body. The following is a list of zirconia pre-sintered bodies used in Examples and Comparative Examples, and their suitable firing temperatures.

Noritake KATANA™ zirconia KT (suitable firing temperature: 1,375° C.; manufactured by Kuraray Noritake Dental Inc.)

Noritake KATANA™ zirconia HT/ML (suitable firing temperature: 1,500° C.; manufactured by Kuraray Noritake Dental Inc.)

Noritake KATANA™ zirconia STML (suitable firing temperature: 1,550° C.; manufactured by Kuraray Noritake Dental Inc.)

Noritake KATANA™ zirconia UTML (suitable firing temperature: 1,550° C.; manufactured by Kuraray Noritake Dental Inc.)

Bellezza Hi-Trans Zirconia (suitable firing temperature: 1,450° C.; manufactured by Nissin Dental Products Inc.)

Measurement of Coefficient of Thermal Expansion of Base Material Formed of Zirconia Sintered Body The coefficient of thermal expansion of a zirconia sintered body was measured in compliance with ISO 6872:2015. The coefficient of thermal expansion was analyzed in a temperature range of 25° C. to 500° C. Specimens were fabricated in the manner described below. Zirconia pre-sintered bodies were prepared using Noritake KATANA™ zirconia HT/ML, Noritake KATANA™ zirconia STML, and Noritake KATANA™ zirconia UTML (zirconia discs manufactured by Kuraray Noritake Dental Inc.), and Bellezza Hi-Trans Zirconia (a zirconia disc manufactured by Nissin Dental Products Inc.). A zirconia block Noritake KATANA™ zirconia KT (20.0 mm×40.0 mm×75.0 mm; manufactured by Kuraray Noritake Dental Inc.) was also prepared as a zirconia pre-sintered body. The zirconia pre-sintered bodies were separately fired for 120 minutes at their suitable firing temperatures to produce zirconia sintered bodies as specimens for coefficient of thermal expansion measurement. The coefficient of thermal expansion was measured in the same manner as in the measurement of the coefficient of thermal expansion of porcelain described above. The measurement results are presented in Table 2.

Examples 1 to 9 and Comparative Examples 1 to 5:
Measurement of Fracture Toughness Value of
Porcelain Layer, and Evaluation of Presence or
Absence of Chipping For the measurement of the fracture toughness value of a porcelain layer, a composite of base material (zirconia sintered body) and porcelain layer was fabricated as a specimen corresponding to a dental product of the present invention. First, a commercially available zirconia pre-sintered body containing yttria as a stabilizer (Noritake KATANA™ zirconia HT/ML, manufactured by Kuraray Noritake Dental Inc.) was cut into a plate shape (measuring about 20 mm in length, about 20 mm in width, and about 1.5 mm in thickness). For preparation of a zirconia sintered body, the zirconia pre-sintered body was fired for 120 minutes at its suitable firing temperature by increasing temperature from room temperature, using Noritake KATANA™ F-1N, a furnace manufactured by SK medical electronics Co., Ltd. One surface of the zirconia sintered body was sandblasted with 50 μm alumina particles under 0.2 MPa pressure as a preparation for the formation of a porcelain layer on the zirconia sintered body. The sandblasting produced a matte surface. The base material was then subjected to ultrasonic washing in acetone, and dried.

In order to form a porcelain layer on the zirconia sintered body, a slurry of the porcelain powder obtained in each Production Example was prepared, and applied onto the zirconia sintered body in a thickness that becomes at least 100 μm greater than the porcelain thickness shown in Table 2 after firing. The porcelain was then fired in a test carried out at the firing temperature and for the time period shown in Table 2. After firing, the porcelain layer was adjusted into dimensions with the thickness shown in Table 2, and was finished by grinding the surface with #2000 sandpaper to prepare a specimen a composite of base material (zirconia sintered body) and porcelain layer. The specimen was used for the measurement of the fracture toughness value of the porcelain layer, which was carried out using the indentation fracture (IF) method under a load of 49 N, in compliance with JIS R 1607: 2015. The measured fracture toughness value of the porcelain layer was used to determine whether the specimen was durable enough as a dental product. After the measurement, the surface of the specimen was visually inspected for the presence or absence of chipping. The results are presented in Table 2.

Examples 1 to 9 and Comparative Examples 1 to 5: Evaluation of Aesthetic Quality, and Evaluation of the Presence or Absence of Cracking A zirconia sintered body frame was fabricated for evaluations of aesthetic quality and the presence or absence of cracking. A molding material, or an impression material as it is also called, was used to take a negative imprint of an abutment tooth and its opposing tooth and surrounding dentition. A plaster was poured into the imprint to fabricate a positive plaster cast, in order to reproduce the abutment tooth and its opposing tooth and surrounding dentition. Thereafter, a wax was used to form a wax crown on the abutment tooth of the plaster cast, with adjusted occlusion, shape, and dimensions. The wax crown serves as the base of frame formation. A surface of the wax crown was then ground to a depth of about 0.2 mm in a frame region to be coated with porcelain. This was followed by taking an optical scan of the abutment tooth and wax crown of the plaster cast with a KATANA™ dental scanner D750 (manufactured by Kuraray Noritake Dental Inc.) to obtain three-dimensional digital data of the abutment tooth and wax crown. Instead of taking an optical scan of the plaster cast as in this example, an intraoral scanner may be used to directly take an intraoral optical scan. Instead of using a wax crown, three-dimensional data based on a virtual frame shape may be created using three-dimensional CAD software after taking an optical scan of the plaster cast.

By using the three-dimensional data, a frame made of a zirconia pre-sintered body was fabricated from Noritake KATANA™ zirconia HT/ML (a zirconia disc manufactured by Kuraray Noritake Dental Inc.), using Noritake KATANA™DWX-50N. The frame was fired at its suitable firing temperature for 120 minutes to fabricate a zirconia sintered body. One surface of the zirconia sintered body was sandblasted with 50 μm alumina particles under 0.2 MPa pressure as a preparation for the formation of a porcelain layer on the zirconia sintered body. The sandblasting produced a matte surface. The frame was then subjected to ultrasonic washing in acetone, and dried.

In order to form a porcelain layer on the zirconia sintered body frame, a slurry of the porcelain powder obtained in each Production Example was prepared, and applied onto the zirconia sintered body frame in a thickness that becomes at least 100 μm greater than the porcelain thickness shown in Table 2 after firing. The porcelain was then fired into a specimen in a test carried out at the firing temperature and for the time period shown in Table 2, using Noritake KATANA™ F-1N, a furnace manufactured by SK medical electronics Co., Ltd. The specimen surface was then observed by visual inspection to evaluate its aesthetic quality and the presence or absence of cracking. In the evaluation of aesthetic quality, the specimen was determined as being "Desirable" when it did not appear cloudy after firing, and "Undesirable" when the specimen after firing was visibly cloudy. The results are presented in Table 2.

Examples 10 to 18 and Comparative Examples 6 and 7: Measurement of Fracture Toughness Value of Porcelain Layer, and Evaluation of Presence or Absence of Chipping For the measurement of the fracture toughness value of a porcelain layer, a composite of base material (zirconia sintered body) and porcelain layer was fabricated as a specimen corresponding to a dental product of the present invention. First, a commercially available zirconia pre-sintered body containing yttria as a stabilizer was cut into a plate shape (measuring about 20 mm in length, about 20 mm in width, and about 1.5 mm in thickness), using Noritake KATANA™ zirconia KT, Noritake KATANA™ zirconia HT/ML, Noritake KATANA™ zirconia STML, Noritake KATANA™ zirconia UTML (all manufactured by Kuraray Noritake Dental Inc.), and Bellezza Hi-Trans Zirconia (manufactured by Nissin Dental Products Inc.). In order to form a porcelain layer on the cut plate of each zirconia pre-sintered body, a slurry of the porcelain powder obtained in each Production Example was prepared, and applied to the plate in a thickness that becomes at least 100 μm greater than the porcelain thickness shown in Table 2 after firing. The zirconia pre-sintered body was then fired for 120 minutes at a temperature equal to or greater than its suitable firing temperature, specifically, at the temperature shown in Table 2, by increasing temperature from room temperature, using Noritake KATANA™ F-1N, a furnace manufactured by SK medical electronics Co., Ltd. Here, the porcelain layer was also fired at the same time. The porcelain layer fired on the zirconia sintered body was adjusted into dimensions with the thickness shown in Table 2, and was finished by grinding the surface with #2000 sandpaper to prepare a specimen a composite of base material (zirconia sintered body) and porcelain layer. The specimen was used for the measurement of the fracture toughness value of the porcelain layer, which was carried out using the indentation fracture (IF) method under a load of 49 N, in compliance with JIS R 1607: 2015. The measured fracture toughness value of the porcelain layer was used to determine whether the specimen was durable enough as a dental product. After the measurement, the surface of the specimen was visually inspected for the presence or absence of chipping. The results are presented in Table 2.

Examples 10 to 18 and Comparative Examples 6 and 7: Evaluations of Aesthetic Quality and the Presence or Absence of Cracking For evaluations of aesthetic quality and the presence or absence of cracking, a zirconia pre-sintered body frame as an underlying structure of a dental product is fabricated in the manner described in Examples 1 to 9 and Comparative Examples 1 to 5, except that the zirconia pre-sintered body is not fired at this stage. A slurry of the porcelain powder obtained in each Production Example was prepared, and applied onto the zirconia pre-sintered body frame in a thickness that becomes at least 100 μm greater than the porcelain thickness shown in Table 2 after firing. The zirconia pre-sintered body was then fired into a specimen in a test carried out at the firing temperature and for the time period shown in Table 2, using Noritake KATANA™ F-1N, a furnace manufactured by SK medical electronics Co., Ltd. Here, the porcelain layer was also fired at the same time. The specimen surface was then observed by visual inspection to evaluate its aesthetic quality and the presence or absence of cracking. In the evaluation of aesthetic quality, the specimen was determined as being "Desirable" when it did not appear cloudy after firing, and "Undesirable" when the specimen after firing was visibly cloudy. The results are presented in Table 2.

zirconia pre-sintered body, it was possible to obtain aesthetically desirable dental products having a desirable fracture toughness value of 1.25 to 2.67 MPa·m$^{0.5}$ with no chipping or cracking, regardless of the suitable firing temperature of the zirconia pre-sintered body.

In Examples 16 to 18 in which the porcelain used for the porcelain layer had a suitable firing temperature of 1,200 to 1,450° C. in producing a dental product by simultaneously firing the zirconia pre-sintered body and the porcelain layer formed on the zirconia pre-sintered body, it was possible to obtain aesthetically desirable dental products having a desirable fracture toughness value of 1.97 to 2.67 MPa·m$^{0.5}$ with no chipping or cracking.

TABLE 2

| | Specifications | | | | | | | | Evaluation results | | |
|---|---|---|---|---|---|---|---|---|---|---|---|
| | Method of manufacture *1 | Suitable firing temperature of zirconia pre-sintered body (° C.) | Porcelain layer | Suitable firing temperature of porcelain (° C.) | CTE difference between zirconia sintered body and porcelain layer (10$^{-6}$K$^{-1}$) | Test firing temperature (° C.) | Test duration (min) | Thickness of porcelain layer (μm) | Fracture toughness value of porcelain layer (MPa·m$^{0.5}$) | Chipping | Aesthetic quality | Cracking |
| Example 1 | (1) | 1500 | Production Example 2 | 1350 | 2.8 | 1500 | 120 | 30 | 2.53 | Absent | Desirable | Absent |
| Example 2 | (1) | 1500 | Production Example 2 | 1350 | 2.8 | 1500 | 120 | 40 | 2.36 | Absent | Desirable | Absent |
| Example 3 | (1) | 1500 | Production Example 2 | 1350 | 2.8 | 1500 | 120 | 60 | 2.32 | Absent | Desirable | Absent |
| Example 4 | (1) | 1500 | Production Example 2 | 1350 | 2.8 | 1500 | 120 | 200 | 1.73 | Absent | Desirable | Absent |
| Example 5 | (1) | 1500 | Production Example 2 | 1350 | 2.8 | 1350 | 1 | 30 | 2.32 | Absent | Desirable | Absent |
| Example 6 | (1) | 1500 | Production Example 2 | 1350 | 2.8 | 1400 | 1 | 30 | 1.60 | Absent | Desirable | Absent |
| Example 7 | (1) | 1500 | Production Example 2 | 1350 | 2.8 | 1450 | 1 | 30 | 1.65 | Absent | Desirable | Absent |
| Example 8 | (1) | 1500 | Production Example 2 | 1350 | 2.8 | 1500 | 1 | 30 | 1.87 | Absent | Desirable | Absent |
| Example 9 | (1) | 1500 | Production Example 2 | 1350 | 2.8 | 1600 | 1 | 30 | 1.38 | Absent | Desirable | Absent |
| Example 10 | (2) | 1375 | Production Example 2 | 1350 | 3.4 | 1375 | 120 | 30 | 1.38 | Absent | Desirable | Absent |
| Example 11 | (2) | 1375 | Production Example 2 | 1350 | 3.4 | 1600 | 120 | 30 | 1.97 | Absent | Desirable | Absent |
| Example 12 | (2) | 1500 | Production Example 2 | 1350 | 2.8 | 1500 | 120 | 30 | 2.67 | Absent | Desirable | Absent |
| Example 13 | (2) | 1450 | Production Example 2 | 1350 | 2.9 | 1450 | 120 | 30 | 1.25 | Absent | Desirable | Absent |
| Example 14 | (2) | 1550 | Production Example 2 | 1350 | 2.7 | 1550 | 120 | 30 | 2.36 | Absent | Desirable | Absent |
| Example 15 | (2) | 1550 | Production Example 2 | 1350 | 2.6 | 1550 | 120 | 30 | 2.64 | Absent | Desirable | Absent |
| Example 16 | (2) | 1500 | Production Example 3 | 1200 | 3.8 | 1500 | 120 | 30 | 1.97 | Absent | Desirable | Absent |
| Example 17 | (2) | 1500 | Production Example 2 | 1350 | 2.8 | 1500 | 120 | 30 | 2.67 | Absent | Desirable | Absent |
| Example 18 | (2) | 1500 | Production Example 1 | 1450 | 4.5 | 1500 | 120 | 30 | 2.31 | Absent | Desirable | Absent |
| Com. Ex. 1 | (1) | 1500 | Production Example 4 | 800 | 1.0 | 800 | 1 | 30 | 0.95 | Present | Desirable | Absent |
| Com. Ex. 2 | (1) | 1500 | Production Example 4 | 800 | 1.0 | 1050 | 1 | 30 | 0.76 | Present | Undesirable | Absent |
| Com. Ex. 3 | (1) | 1500 | Production Example 2 | 1350 | 2.8 | 1300 | 1 | 30 | 1.09 | Absent | Undesirable | Absent |
| Com. Ex. 4 | (1) | 1500 | Production Example 2 | 1350 | 2.8 | 1325 | 1 | 30 | 1.06 | Absent | Undesirable | Absent |
| Com. Ex. 5 | (1) | 1500 | Production Example 5 | 850 | 1.1 | 1500 | 120 | 30 | Unmeasurable | Present | Undesirable | Absent |
| Com. Ex. 6 | (2) | 1500 | Production Example 4 | 800 | 1.0 | 1500 | 120 | 30 | 2.27 | Absent | Undesirable | Present |
| Com. Ex. 7 | (2) | 1500 | Production Example 5 | 850 | 1.1 | 1500 | 120 | 30 | Unmeasurable | Present | Undesirable | Present |

*1 Note on method of manufacture:
Method of manufacture (1) is a method that forms a porcelain layer on a zirconia sintered body, and fires the porcelain layer.
Method of manufacture (2) is a method that forms a porcelain layer on a zirconia pre-sintered body, and fires the zirconia pre-sintered body and the overlying porcelain layer at the same time.

In Examples 1 to 9 in which the porcelain layer was formed on the zirconia sintered body, and fired at a temperature of 1,350° C. or more, it was possible to obtain aesthetically desirable dental products having a desirable fracture toughness value of 1.38 to 2.53 MPa·m$^{0.5}$ with no chipping or cracking, regardless of the duration of firing.

In Examples 10 to 15 in which the zirconia pre-sintered body and the porcelain layer formed on the zirconia pre-sintered body were fired at the same time at a temperature equal to or greater than the suitable firing temperature of the In Comparative Example 1, the porcelain layer had no observable cracks, and there was no aesthetic issue due to cloudiness. However, the porcelain layer had a low fracture toughness value, and chipping was observed in the porcelain layer, making it unsuitable as a dental product.

In Comparative Example 2, the porcelain layer had an aesthetic issue due to cloudiness, though cracks were not observed. The porcelain layer also had a notably low fracture toughness value, and chipping was observed in the porcelain layer, making it unsuitable as a dental product.

In Comparative Examples 3 and 4, the porcelain layer had an aesthetic issue due to cloudiness, though cracks were not observed. However, the porcelain layer had a low fracture toughness value, and was unsuitable as a dental product, despite that chipping was not observed.

In Comparative Example 5 based on Production Example 5 corresponding to Patent Literature 2 (JP 2017-122064 A), the porcelain layer had an aesthetic issue due to cloudiness, though cracking was not observed. The porcelain layer also had chipping so serious that the fracture toughness value was almost unmeasurable, making the porcelain layer unsuitable as a dental product.

In Comparative Example 6, the porcelain layer had not observable chipping, and showed a desirable fracture toughness value. However, the porcelain layer was unsuitable as a dental product because of the aesthetically problematic cloudiness observed in the dental product tested, and the cracks observed in the porcelain layer.

In Comparative Example 7 based on Production Example 5 corresponding to Patent Literature 2 (JP 2017-122064 A), cracks and fractures were observed in the porcelain layer, and the porcelain layer had an aesthetic issue due to cloudiness. The porcelain layer also had chipping so serious that the fracture toughness value was almost unmeasurable, making the porcelain layer unsuitable as a dental product.

INDUSTRIAL APPLICABILITY

A dental product of the present invention has high aesthetic quality, and the porcelain layer of the dental product has high fracture toughness and desirable resistance against chipping, detachment, and cracking. This makes a dental product of the present invention usable as at least one selected from the group consisting of a dental prosthesis, an orthodontic product, and a product for dental implants.

REFERENCE SIGNS LIST

1 Zirconia pre-sintered body
2 Zirconia sintered body
3 Porcelain layer

The invention claimed is:

1. A dental product comprising:
a base material formed of a zirconia sintered body; and
a porcelain layer formed by sintering porcelain,
wherein the porcelain comprises ceramic, glass, or glass-ceramic, and comprises 65.0 to 90.0 mol % of $SiO_2$, 4.0 to 15.0 mol % of $Al_2O_3$, 0.1 to 10.0 mol % of $Na_2O$, 1.0 to 10.0 mol % of $K_2O$, and 0.01 to 15.0 mol % of CaO, and optionally less than 0.1 mol % of $Li_2O$ based on total 100 mol % of constituent components. and has a suitable firing temperature of 1050° C. or more, and the porcelain layer has a fracture toughness value of 1.20 MPa·m$^{0.5}$ or more.

2. The dental product according to claim 1, wherein the porcelain layer has a thickness of 10 to 500 μm.

3. The dental product according to claim 1, wherein the base material formed of a zirconia sintered body comprises a stabilizer.

4. The dental product according to claim 3, wherein the stabilizer is at least one selected from the group consisting of yttrium oxide, titanium oxide, calcium oxide, magnesium oxide, cerium oxide, aluminum oxide, scandium oxide, lanthanum oxide, erbium oxide, praseodymium oxide, samarium oxide, europium oxide, and thulium oxide.

5. The dental product according to claim 1, wherein the suitable firing temperature of the porcelain is 1,100° C. or more.

6. The dental product according to claim 1, wherein the dental product satisfies the following relation,
0<{(coefficient of thermal expansion of the porcelain)/ (coefficient of thermal expansion of the zirconia sintered body)}<1.0.

7. The dental product according to claim 6, wherein the dental product satisfies the following relation,
$1.0 \times 10^{-6} K^{-1} \leq$ (coefficient of thermal expansion of the zirconia sintered body) - (coefficient of thermal expansion of the porcelain)$\leq 4.5 \times 10^{-6} K^{-1}$.

8. A method for manufacturing the dental product of claim 1, comprising forming a porcelain layer on a zirconia sintered body, and firing the porcelain layer at a temperature of 1,350° C. or more.

9. A method for manufacturing the dental product of claim 1, comprising forming a porcelain layer on a zirconia pre-sintered body, and firing the zirconia pre-sintered body and the porcelain layer at a temperature equal to or greater than a suitable firing temperature of the zirconia pre-sintered body.

10. The dental product according to claim 1, wherein the dental product is a dental prosthesis, an orthodontic product, or a product for dental implants.

11. The dental product according to claim 1, wherein the porcelain of the porcelain layer comprises, based on total 100 mol % of constituent components,
67.0 to 89.5 mol % of $SiO_2$,
5.6 to 14.5 mol % of $Al_2O_3$,
1.0 to 7.0 mol % of $Na_2O$,
2.5 to 9.5 mol % of $K_2O$, and
0.05 to 13.5 mol % of CaO.

12. The dental product according to claim 1, wherein the porcelain of the porcelain layer comprises, based on total 100 mol % of constituent components,
69.8 to 88.7 mol % of $SiO_2$,
5.7 to 12.7 mol % of $Al_2O_3$,
1.7 to 3.8 mol % of $Na_2O$,
3.6 to 8.3 mol % of $K_2O$, and
0.1 to 12.2 mol % of CaO.

13. The dental product according to claim 1, wherein the porcelain of the porcelain layer satisfies
1.0<{(number of moles of $K_2O$)/(number of moles of $Na_2O$)};.

* * * * *